United States Patent
Schultz et al.

(10) Patent No.: US 6,388,037 B2
(45) Date of Patent: May 14, 2002

(54) ALLYLATED AMIDE COMPOUNDS AND DIE ATTACH ADHESIVES PREPARED THEREFROM

(75) Inventors: Rose Ann Schultz, Westford, MA (US); Donald E. Herr, Doylestown, PA (US); Chaodong Xiao, East Hanover, NJ (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 0 days.

(21) Appl. No.: 09/801,851

(22) Filed: Jun. 29, 2001

Related U.S. Application Data

(62) Division of application No. 09/336,082, filed on Jun. 18, 1999.
(60) Provisional application No. 60/091,509, filed on Jul. 2, 1998.

(51) Int. Cl.$^7$ .............................................. C08F 120/54
(52) U.S. Cl. .................... 526/305; 526/303.1; 526/306; 526/310; 526/312
(58) Field of Search .............................. 526/303.1, 305, 526/306, 310, 312

(56) References Cited

U.S. PATENT DOCUMENTS

| | | | |
|---|---|---|---|
| 4,021,224 A | * 5/1977 | Pallos et al. ................... 71/88 |
| 4,311,636 A | 1/1982 | Hahn et al. ................ 260/45.8 |
| 4,336,311 A | 6/1982 | Lucey ........................ 428/521 |
| 4,485,218 A | 11/1984 | Bell et al. ................... 525/257 |
| 4,533,975 A | 8/1985 | Bill ............................ 361/323 |
| 4,613,637 A | 9/1986 | Landis et al. ............... 524/105 |
| 4,623,559 A | 11/1986 | Hudock ..................... 427/54.1 |
| 4,663,424 A | 5/1987 | Stix et al. ................... 528/182 |
| 4,720,445 A | 1/1988 | Brahim et al. .............. 430/192 |
| 4,826,995 A | 5/1989 | Alexander et al. .......... 548/521 |
| 4,876,358 A | 10/1989 | Alexander ................. 548/521 |
| 4,980,436 A | 12/1990 | Saito et al. ................. 526/261 |
| 4,999,136 A | 3/1991 | Su et al. ..................... 252/512 |
| 5,017,406 A | 5/1991 | Lutz .......................... 427/54.1 |
| 5,137,936 A | 8/1992 | Akiguchi et al. ........... 522/170 |
| 5,258,426 A | 11/1993 | Uchida et al. .............. 523/435 |
| 5,272,377 A | 12/1993 | Shimozawa et al. ........ 257/787 |
| 5,314,950 A | 5/1994 | Singh et al. .................. 525/73 |
| 5,347,258 A | 9/1994 | Howard et al. ............. 338/333 |
| 5,426,008 A | 6/1995 | Hagiwara et al. ............. 430/18 |
| 5,532,296 A | 7/1996 | Recker et al. .............. 523/400 |
| 5,602,205 A | 2/1997 | Singh et al. ................ 525/282 |
| 5,627,222 A | 5/1997 | Recker et al. .............. 523/400 |
| 5,726,391 A | 3/1998 | Iyer et al. .................. 174/52.2 |
| 5,760,337 A | 6/1998 | Iyer et al. .................. 174/52.2 |
| 5,863,664 A | 1/1999 | McCormick et al. ....... 428/500 |

FOREIGN PATENT DOCUMENTS

| | | | |
|---|---|---|---|
| EP | 0 051 165 | 5/1982 | ........... H01L/23/14 |
| EP | 0 357 110 | 3/1990 | ......... C09D/151/00 |
| EP | 0 475 655 A2 | 3/1992 | ............ C08K/9/10 |
| JP | 1-1582174 | 12/1987 | ............ C09D/5/44 |
| JP | 4-146984 | 5/1992 | .......... C09J/133/08 |
| JP | 10-168413 | 6/1998 | |
| WO | WO 96/07691 | 3/1996 | ........... C08G/73/10 |
| WO | WO 97/18254 | 5/1997 | ........... C08G/73/12 |

OTHER PUBLICATIONS

Mark A. Smith et al., "Bismaleimide/Vinyl Ether Matrix Copolymers", Department of Chemistry and Center for Macromolecular Science and Engineering, Univ. of Florida, Gainesville, FL (2 pgs.).

Carol K. Sauers, "The Dehydration of N–Arylmaleamic Acids with Acetic Anhydride", The Journal of Organic Chemistry, vol. 34, No. 8, Aug. 1969, pp. 2275–2279.

Robert J. Cotter et al., "The Synthesis of N–Substituted isomaleimides", vol. 26, Jan. 1961, pp. 10–15.

* cited by examiner

*Primary Examiner*—Helen L. Pezzuto
(74) *Attorney, Agent, or Firm*—Jane E. Gennaro

(57) ABSTRACT

Allylated amide compounds are formulated into curable compositions with a free radical curing agent, and optionally, one or more fillers, for use as adhesives in the manufacture of microelectronic devices.

2 Claims, No Drawings

ALLYLATED AMIDE COMPOUNDS AND DIE ATTACH ADHESIVES PREPARED THEREFROM

This is a divisional of U.S. patent application Ser. No. 09/336,082, filed Jun. 18, 1999 pending.

The priority of provisional application 60/091,509, filed Jul. 2, 1998, is claimed under 35 USC 119(e).

FIELD OF THE INVENTION

This invention relates to allylated amide compounds and adhesives prepared from those compounds.

BACKGROUND OF THE INVENTION

Adhesive compositions, particularly conductive adhesives, are used for a variety of purposes in the fabrication and assembly of semiconductor packages and microelectronic devices. The more prominent uses are the bonding of integrated circuit chips to lead frames or other substrates, and the bonding of circuit packages or assemblies to printed wire boards.

The requirements for conductive adhesives in electronic packaging are that they have good mechanical strength, curing properties that do not affect the component or the carrier, and thixotropic properties compatible with existing application equipment currently used in the industry.

Another important aspect of an adhesive bonding or interconnection technology is the ability to rework the bond. For single chip packaging involving high volume commodity products, a failed chip can be discarded without significant loss. However, it becomes expensive to discard multichip packages with only one failed chip; consequently, the ability to rework the failed chip would be a manufacturing advantage. Today, one of the primary thrusts within the semiconductor industry is to develop adhesives that will meet all the requirements for adhesive strength and flexibility, but that will also be reworkable.

Conventional adhesive technology uses low viscosity thermosetting organic materials, the most widely used being epoxy systems. In order to achieve the required mechanical performance, relatively high molecular weight thermoplastics would be the preferred compositions for adhesive materials. These materials, however, have high viscosity or even solid film form, which are drawbacks to the manufacturing process. Therefore, there is a need for new adhesives that are easily dispensable to conform with automated manufacturing processes and that are reworkable.

SUMMARY OF THE INVENTION

This invention relates to allylated amide compounds that can be used in curable compositions. Allylated in this context means that allyl moieties are bonded to the nitrogen of amide moieties.

In another embodiment, this invention is an adhesive composition for use in electronic devices that comprises one or more allylated amide compounds, a curing initiator, and optionally, one or more fillers. The composition optionally may also contain mono- or polyfunctional vinyl compounds.

In another embodiment, this invention is the cured adhesive that results from the just described curable adhesive composition.

In another embodiment, this invention is a electronic assembly comprising an electronic component bonded to a substrate with a cured adhesive composition prepared from a composition comprising one or more allylated amide compounds, a curing initiator, optionally one or more fillers, and optionally one or more mono- or polyfunctional vinyl compounds.

In another embodiment, this invention is a method for adhering an electronic component to a substrate with a cured adhesive prepared from a composition comprising one or more allylated amide compounds, a curing initiator, optionally one or more fillers, and optionally, one or more mono- or polyfunctional vinyl compounds, the method comprising applying the adhesive to the component or the substrate, contacting the component and the substrate, and curing the adhesive in situ.

DETAILED DESCRIPTION OF THE INVENTION

The allylated amide compounds, and vinyl compounds, used in the adhesive compositions of this invention are curable compounds, meaning that they are capable of polymerization, with or without crosslinking. As used in this specification, to cure will mean to polymerize, with or without crosslinking. Cross-linking, as is understood in the art, is the attachment of two polymer chains by bridges of an element, a molecular group, or a compound, and in general will take place upon heating. As cross-linking density is increased, the properties of a material can be changed from thermoplastic to thermosetting.

It is possible to prepare polymers of a wide range of cross-link density by the judicious choice and amount of mono- or polyfunctional compounds. The greater proportion of polyfunctional compounds reacted, the greater the cross-link density. In order to provide thermoplastic properties, adhesive compositions are prepared from mono-functional compounds to limit the cross-link density. However, a minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

The cross-link density can also be controlled to give a wide range of glass transition temperatures in the cured adhesive to withstand subsequent processing and operation temperatures.

In those cases where it is necessary to rework the assembly, the electronic component can be pried off the substrate, and any residue adhesive can be heated until it softens and is easily removed.

In the inventive adhesive compositions, the allylated amide compounds, and vinyl compounds if used in combination with the allylated amide compounds, will be present in the curable package adhesive compositions in an amount from 2 to 98 weight percent based on the organic components present (excluding any fillers).

The adhesive compositions will further comprise at least one free-radical initiator, which is defined to be a chemical species that decomposes to a molecular fragment having one or more unpaired electrons, highly reactive and usually short-lived, which is capable of initiating a chemical reaction by means of a chain mechanism. The free-radical initiator will be present in an amount of 0.1 to 10 percent, preferably 0.1 to 3.0 percent, by weight of the allylated amide compound, or combination of both allylated amide and vinyl compounds (excluding any filler). The free radical curing mechanism gives a fast cure and provides the composition with a long shelf life before cure. Preferred free-radical initiators include peroxides, such as butyl peroctoates and dicumyl peroxide, and azo compounds, such as 2,2'-azobis(2-methyl-propanenitrile) and 2,2'-azobis(2-methyl-butanenitrile).

Alternatively, the adhesive compositions may contain a photoinitiator, such as is sold by Ciba Specialty Chemicals under the trademark Irgacure, in lieu of the free-radical initiator, and the curing process may then be initiated by UV radiation. The photoinitiator will be present in an amount of 0.1 to 10 percent, preferably 0.1 to 3.0 percent, by weight of the allylated amide compound, or combination of both allylated amide and vinyl compounds (excluding any filler). In some cases, both photoinitiation and free-radical initiation may be desirable. For example, the curing process can be started by UV irradiation, and in a later processing step, curing can be completed by the application of heat to accomplish a free-radical cure.

In general, these compositions will cure within a temperature range of 50° to 250° C., and curing will be effected within a length of time of less than one minute to four hours. As will be understood, the time and temperature curing profile for each adhesive composition will vary, and different compositions can be designed to provide the curing profile that will be suited to the particular industrial manufacturing process.

Ease of application, even when thermoplastic properties are desired for the adhesive, is achieved by using relatively low molecular weight reactive oligomers or pre-polymers and curing these in situ after application to the electronic component or substrate. Applying the materials in an uncured state gives high processibility, and the resultant cured thermoplastic adhesive provides high mechanical performance.

Suitable conductive fillers for the adhesives are silver, copper, gold, palladium, platinum.

Allylated Amide Compounds

The allylated amide compounds suitable for use in the compositions of this invention have a structure represented by the formulas A and B as depicted here:

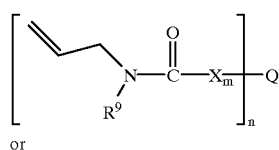

(A)

or

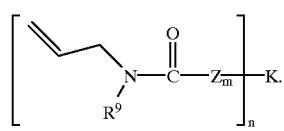

(B)

As used throughout this specification, the notation C(O) refers to a carbonyl group. For these specific formulae, when lower case "n" is the integer 1, the compound will be a mono-functional compound; and when lower case "n" is an integer 2 to 6, the compound will be a poly-functional compound.

Formula A represents those compounds in which:

$R^9$ is H, an alkyl or alkyleneoxy group having 1 to 18 carbon atoms, allyl, aryl, or substituted aryl having the structure

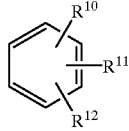

in which $R^{10}$, $R^{11}$, and $R^{12}$ are independently H or an alkyl or alkyleneoxy group having 1 to 18 carbon atoms;

each X independently is an aromatic group selected from the aromatic groups having the structures (I) through (V):

(I)

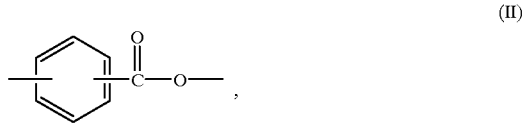

(II)

(III)

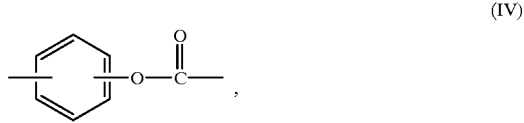

(IV)

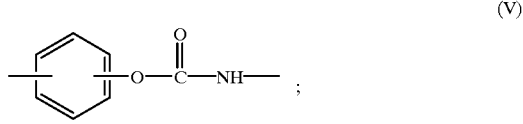

(V)

and Q is a linear or branched chain alkyl, alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to X;

or Q is a urethane having the structure:

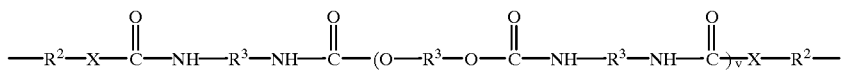

in which each $R^2$ independently is an alkyl, aryl, or arylalkyl group having 1 to 18 carbon atoms; $R^3$ is an alkyl or alkyloxy chain having up to 100 atoms in the chain, which chain may contain aryl substituents; X is O, S, N, or P; and v is 0 to 50;

or Q is an ester having the structure:

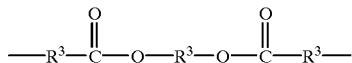

in which $R^3$ is an alkyl or alkyloxy chain having up to 100 atoms in the chain, which chain may contain aryl substituents;

or Q is a siloxane having the structure: $-(CR^1{}_2)_e-[SiR^4{}_2-O]_f-SiR^4{}_2-(CR^1{}_2)_g-$ in which the $R^1$ substituent independently for each position is H or an alkyl group having 1 to 5 carbon atoms and the $R^4$ substituent independently for each position is an alkyl group having 1 to 5 carbon atoms or an aryl group, and e and g are independently 1 to 10 and f is 1 to 50; and m is 0 or 1, and n is 1 to 6.

Formula B represents those compounds in which $R^9$ is H, or an alkyl or alkyleneoxy group having 1 to 18 carbon atoms, or an allyl group, or an aryl or substituted aryl having the structure

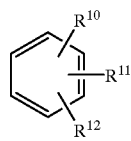

in which $R^{10}$, $R^{11}$, and $R^{12}$ are independently H or an alkyl or alkyleneoxy group having 1 to 18 carbon atoms;

Z is a linear or branched chain alkyl, alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to K;

or Z is a urethane having the structure:

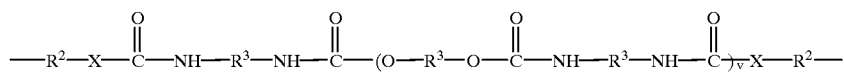

in which each $R^2$ independently is an alkyl, aryl, or arylalkyl group having 1 to 18 carbon atoms; $R^3$ is an alkyl or alkyloxy chain having up to 100 atoms in the chain, which chain may contain aryl substituents; X is O, S, N, or P; and v is 0 to 50;

or Z is an ester having the structure:

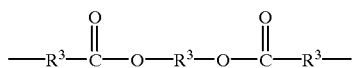

in which $R^3$ is an alkyl or alkyloxy chain having up to 100 atoms in the chain, which chain may contain aryl substituents;

or Z is a siloxane having the structure:

$-(CR^1{}_2)_e-[SiR^4{}_2-O]_f-SiR^4{}_2-(CR^1{}_2)_g-$ in which the $R^1$ substituent independently for each position is H or an alkyl group having 1 to 5 carbon atoms and the $R^4$ substituent independently for each position is an alkyl group having 1 to 5 carbon atoms or an aryl group, and e and g are independently 1 to 10 and f is 1 to 50;

K is an aromatic group selected from the aromatic groups having the structures (VI) through (XIII) (although only one bond may be shown to represent connection to the aromatic group K, this will be deemed to represent any number of additional bonds as described and defined by n):

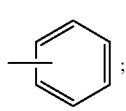
(VI)

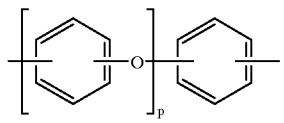
(VII)

in which p is 1 to 100;

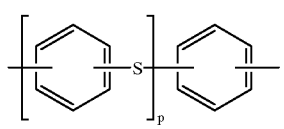
(VIII)

in which p is 1 to 100;

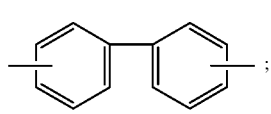
(IX)

-continued

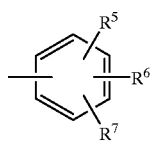
(X)

in which $R^5$, $R^6$, and $R^7$ are a linear or branched chain alkyl alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to the aromatic ring; or $R^5$, $R^6$, and $R^7$ are a siloxane having the structure $—(CR^1{}_2)_e—[SiR^4{}_2—O]_f—SiR^4{}_2—(CH_3)_g—$ in which the $R^1$ substituent is H or an alkyl group having 1 to 5 carbon atoms and the $R^4$ substituent independently for each position is an alkyl group having 1 to 5 carbon atoms or an aryl group, and e is 1 to 10 and f is 1 to 50;

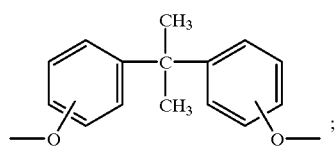
(XI)

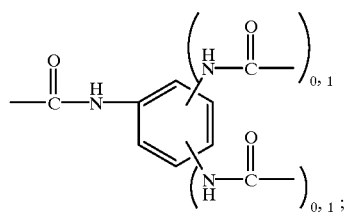
(XII)

and

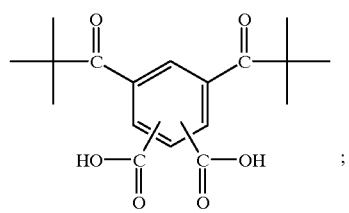
(XIII)

and m is 0 or 1 and n is 1 to 6.

Vinyl Compounds

The compounds suitable for use in the adhesive compositions of this invention have a structure represented by one of the formulae:

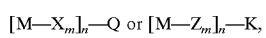

in which m is 0 or 1, and n is 1 to 6.

M represents a vinyl group and can be the maleimide moiety having the structure:

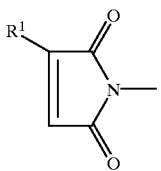

in which $R^1$ is H or $C_1$ to $C_5$ alkyl; or or the vinyl moiety having the structure:

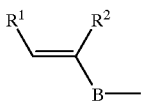

in which $R^1$ and $R^2$ are H or an alkyl having 1 to 5 carbon atoms, or together form a 5 to 9 membered ring with the carbons forming the vinyl group; B is C, S, N, O, C(O), O—C(O), C(O)—O, C(O)NH or C(O)N($R^8$), in which $R^8$ is $C_1$ to $C_5$ alkyl. Preferably, B is O, C(O), O—C(O), C(O)—O, C(O)NH or C(O)N($R^8$); more preferably B is O, C(O), or C(O)N($R^8$).

X independently is an aromatic group selected from the aromatic groups having the structures (I) through (V):

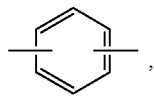
(I)

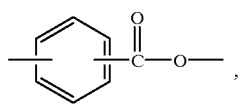
(II)

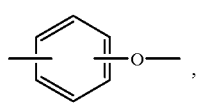
(III)

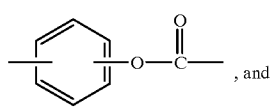
(IV)

, and

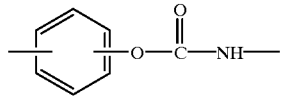
(V)

Preferably, X is structure (II), (III), (IV) or (V), and more preferably is structure (II).

Q and Z independently can be a linear or branched chain alkyl, alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to X;

or Q and Z independently can be a urethane having the structure:

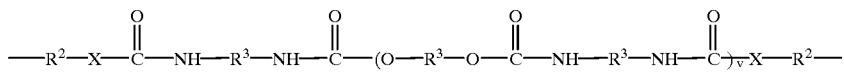

in which each $R^2$ independently is an alkyl, aryl, or arylalkyl group having 1 to 18 carbon atoms; $R^3$ is an alkyl or alkyloxy chain having up to 100 atoms in the chain, which chain may contain aryl substituents; X is O, S, N, or P; and v is 0 to 50;

or Q and Z independently can be an ester having the structure:

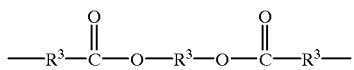

in which $R^3$ is an alkyl or alkyloxy chain having up to 100 atoms in the chain, which chain may contain aryl substituents;

or Q and Z independently can be a siloxane having the structure: $-(CR^1_2)_e-[SiR^4_2-O]_f-SiR^4_2-(CR^1_2)_g-$ in which the $R^1$ substituent independently for each position is H or an alkyl group having 1 to 5 carbon atoms and the $R^4$ substituent independently for each position is an alkyl group having 1 to 5 carbon atoms or an aryl group, and e and g are independently 1 to 10 and f is 1 to 50.

Preferably, Q and Z will be a linear or branched chain alkyl, alkyloxy, alkylene, or alkyleneoxy species having up to about 100 atoms in the chain, as described with pendant saturated or unsaturated cyclic or heterocyclic substituents, or a siloxane as described, and more preferably is a linear or branched chain alkyl species or siloxane, as described.

K is an aromatic group selected from the aromatic groups having the structures (VI) through (XIII) (although only one bond may be shown to represent connection to the aromatic group K, this will be deemed to represent any number of additional bonds as described and defined by n):

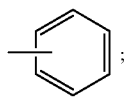
(VI)

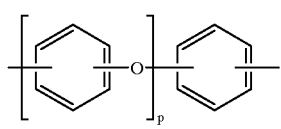
(VII)

in which p is 1 to 100;

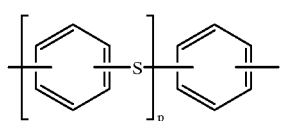
(VIII)

in which p is 1 to 100;

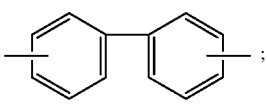
(IX)

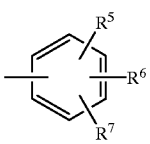
(X)

in which $R^5$, $R^6$, and $R^7$ are a linear or branched chain alkyl, alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to the aromatic ring; or $R^5$, $R^6$, and $R^7$ are a siloxane having the structure $-(CR^1_2)_e-[SiR^4_2-O]_f-SiR^4_2-(CH_3)_g-$ in which the $R^1$ substituent is H or an alkyl group having 1 to 5 carbon atoms and the $R^4$ substituent independently for each position is an alkyl group having 1 to 5 carbon atoms or an aryl group, and e is 1 to 10 and f is 1 to 50;

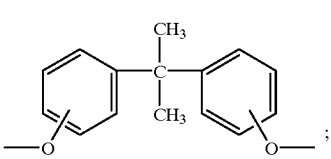
(XI)

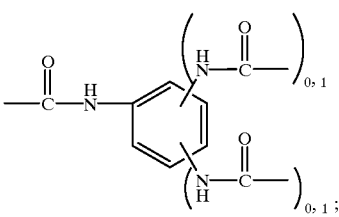
(XII)

and

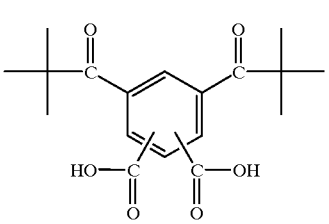
(XIII)

Preferably, K is structure (VIII), (X) or (XI), more preferably is structure (X) or (XI), and most preferably is structure (X).

Other Composition Components

Depending on the nature of the substrate, the composition may also contain a coupling agent. A coupling agent as used herein is a chemical species containing a polymerizable functional group for reaction with the maleimide and other vinyl compound, and a functional group capable of condensing with metal hydroxides present on the surface of the substrate. Such coupling agents and the preferred amounts for use in compositions for particular substrates are known in the art. Suitable coupling agents are silanes, silicate esters, metal acrylates or methacrylates, titanates, and compounds containing a chelating ligand, such as phosphine, mercaptan, and acetoacetate. When present, coupling agents typically will be in amounts up to 10 percent by weight, and preferably in amounts of 0.1 to 3.0 percent by weight, of the allylated armide and vinyl compound, if any.

In addition, the compositions may contain compounds that lend additional flexibility and toughness to the resultant cured composition. Such compounds may be any thermoset or thermoplastic material having a Tg of 50° C. or less, and typically will be a polymeric material characterized by free rotation about the chemical bonds, such as can be obtained by the presence of carbon-carbon double bonds adjacent to carbon-carbon single bonds, the presence of ester and ether groups, and the absence of ring structures. Suitable such modifiers include polyacrylates, poly(butadiene), polyTHF (polymerized tetrahydrofuran), CTBN (carboxy-terminated butyronitrile) rubber, and polypropylene glycol. When present, toughening compounds may be in an amount up to about 15 percent by weight of the maleimide and other monofunctional vinyl compound.

Siloxanes may also be added to the compositions to impart elastomeric properties. Suitable siloxanes are the methacryloxypropyl-terminated polydimethyl siloxanes, and the aminopropyl-terminated polydimethylsiloxanes, available from United Chemical Technologies.

The composition may also contain organic fillers, such as, polymers to adjust rheology. Other additives known and used in the art may also be used for specific purposes, such as, adhesion promoters. The selection of the types and amounts suitable is within the expertise of one skilled in the art.

EXAMPLE 1

Preparation of Bis Phenol F-Bis(diallylamide)

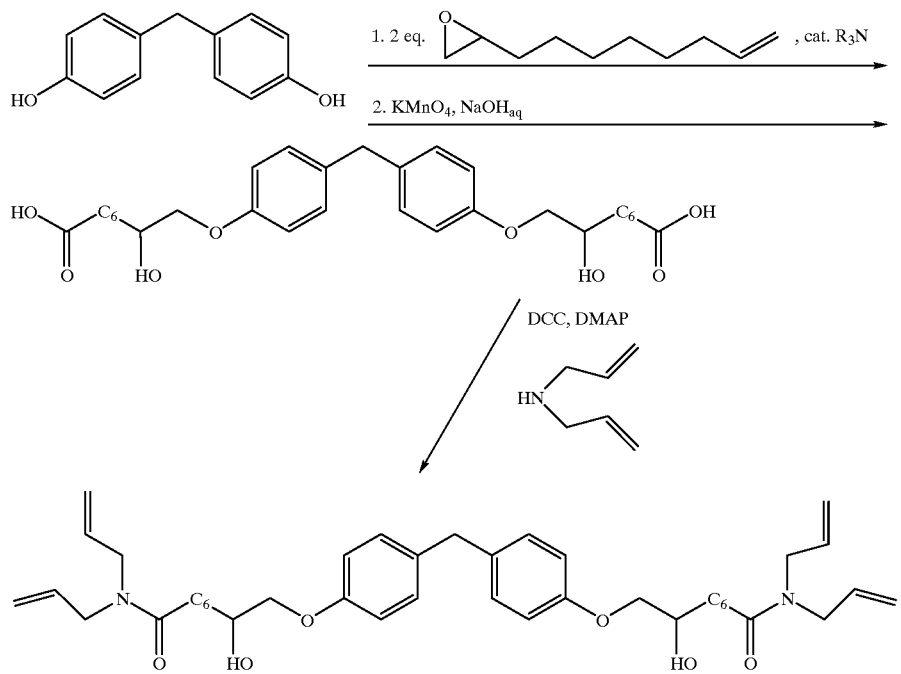

Bisphenol F (200.3 g, 1 mol) is solvated in tetrahydrofuran (THF) (500 mL) in a 2 L three-necked flask equipped with mechanical stirrer and reflux condenser. To this solution is added 1,2-epoxy-9-decene (308.5 g, 2 mol) and benzyldimethylamine (0.67 g, 5 mmol). The solution is warmed to 80° C. for 7 hours and then allowed to cool to room temperature. Solvent is removed in vacuo to yield an oil.

The intermediate isolated above (508.8 g, 1 mol) is dissolved in THF (1 L) and $H_2O$ (1 L) in a 3 L three-necked flask equipped with mechanical stirrer, reflux condenser and internal temperature probe under nitrogen. To this solution is added KMnO4 (316 g, 2 mol), and the resulting mixture warmed to 80° C. for 5 hours. The reaction is allowed to cool to room temperature and bulk solvent is removed in vacuo. The resulting material is solvated in $CH_2Cl_2$ (1 L), filtered, and washed with $H_2O$ (3×1 L). The isolated organics are dried over $MgSO_4$ and solvent removed in vacuo to yield a diacid intermediate.

The above diacid (544.8 g, 1 mol) is combined with diallylamine (194.3 g, 2 mol) and $CH_2Cl_2$ (1 L) in a 3 L three-necked flask equipped with a mechanical stirrer, addition funnel and internal temperature probe under nitrogen. The solution is cooled to 4° C. in an ice bath. The addition funnel is charged with dicyclohexylcarbodiimide (DCC) (412.7 g, 2 mol) dissolved in $CH_2Cl_2$ (300 mL), and this solution added to the stirred amine solution over the course of 60 minutes. The reaction is stirred on the ice bath for an additional 30 minutes. The mixture is allowed to warm to room temperature and further stirred for 4 hours. The solution is filtered to remove precipitated dicyclohexylurea (DCU). The isolated organics are dried over $MgSO_4$ anhyd., filtered and solvent removed in vacuo to yield the bis (diallylamide) product.

EXAMPLE 2

Preparation of Poly(butadiene)bis(diallylamide)

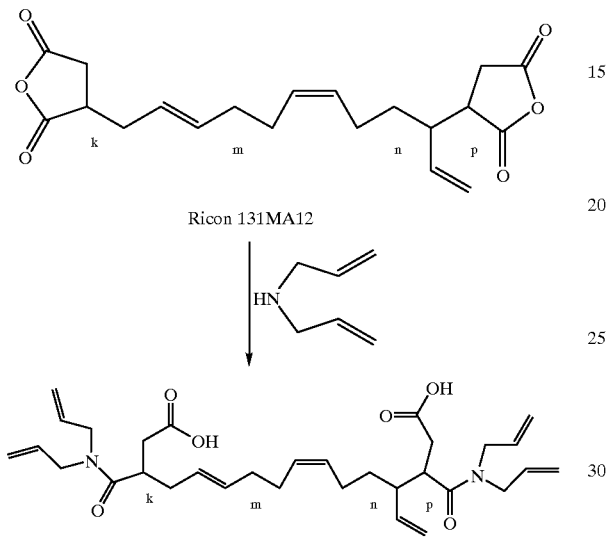

Diallylamine (97.15 g, 1 mol) is solvated in acetone (500 mL) in a 2 L three-necked flask equipped with mechanical stirrer, addition funnel and internal temperature probe under nitrogen. The solution is cooled on an ice bath. Maleinized poly(butadiene) (Ricon 131MA5, Ricon Resins Inc., 1766 g) dissolved in acetone (500 mL) is charged into the addition funnel and added to the cooled amine solution over the course of 60 minutes maintaining an internal temperature<10° C. The solution is stirred on ice for an additional 60 minutes, then allowed to warm to room temperature and stirred for another 2 hours. Solvent and residual diallylamine are removed in vacuo to yield the poly(diallylamide).

EXAMPLE 3

Preparation of Dimer Bis(diallylamide) or 10,11-Dioctyl-1,20-eicosyl Bis(diallylamide)

Dimer acid (sold under the trademark Empol 1024 by Unichema, 20.5 g, 35.7 mmol) was solvated in anhydrous toluene (250 mL) in a 500 mL four-necked flask equipped with reflux condenser, addition funnel, and magnetic stirring under nitrogen. This solution was warmed to 80° C., and oxalyl chloride (12.5 mL, 143 mmol) was added dropwise over the course of 60 minutes. Evolution of $CO_2$, CO and HCl was immediately evident. The reaction was stirred for an additional 3 hours after the addition was complete, allowed to cool to room temperature and solvent removed in vacuo to yield an orange oil. IR and $^1H$ NMR spectral data were consistent with the desired bis(acid chloride) product.

Diallyl amine (10.0 mL) was solvated in diethyl ether ($Et_2O$) (200 mL) in a 500 mL three-necked flask equipped with mechanical stirrer, addition funnel and internal temperature probe under nitrogen. NaOH (3.2 g, 80 mmol) dissolved in $H_2O$ (100 mL) was added to this solution. This solution was cooled to 4° C. on an ice bath. The bis(acid chloride) described above was solvated in $Et_2O$ (20 mL), charged into the addition funnel and added to the stirred amine solution over the course of 30 minutes, maintaining an internal temperature<10° C. This solution was stirred on ice for an additional one hour, then allowed to warm to room temperature, and stirred for an additional 4 hours. The organic layer was isolated and washed with 5% $HCl_{aq}$ (200 mL), and $H_2O$ (2×200 mL). The isolated organics were dried over MgSO4 anhydrous, filtered, and the solvent removed in vacuo to yield an orange oil (87%), which exhibited IR and $^1HNMR$ spectral data consistent with the desired bis (diallylamide).

What is claimed is:
1. A curable composition comprising a curing initiator and an allylated amide compound having the formula

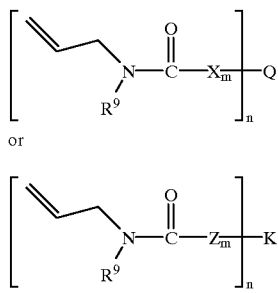

or

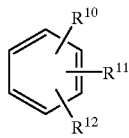

in which m is 0 or 1, n is 1 to 6, and
 (a) $R^9$ is H, an alkyl group having 1 to 18 carbon atoms, an alkyleneoxy group having 1 to 18 carbon atoms, an allyl group, an aryl group, or a substituted aryl group having the structure

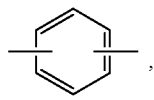

in which $R^{10}$, $R^{11}$, and $R^{12}$ are independently H or an alkyl or alkyleneoxy group having 1 to 18 carbon atoms;
 (b) X is an aromatic group selected from the group of aromatic groups having the structures:

(I)

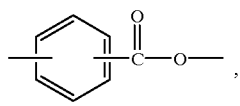

(II)

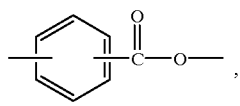

(III)

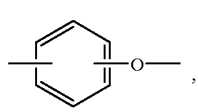

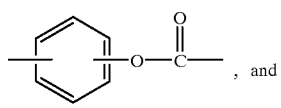
, and (IV)

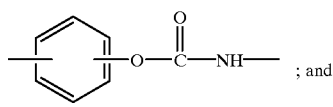
; and (V)

(c) Q is selected from the group consisting of

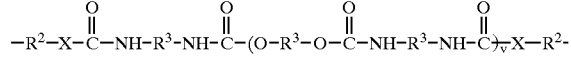
(i)

in which each $R^2$ independently is an alkyl, aryl, or arylalkyl group having 1 to 18 carbon atoms; $R^3$ is an alkyl or alkyloxy chain having up to 100 atoms in the chain, which chain may contain aryl substituents;

X is O, S, N, or P; and v is 0 to 50;

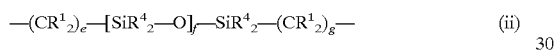
(ii)

in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50;

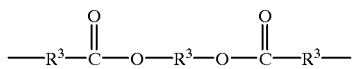
(iii)

in which $R^3$ is an alkyl or alkyloxy chain having up to 100 atoms in the chain, which chain may contain aryl substituents;

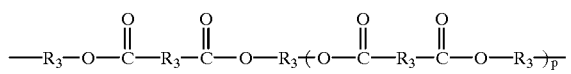
(iv)

in which p is 1 to 100, each $R^3$ is independently an alkyl or alkyloxy chain having up to 100 atoms in the chain, which chain may contain aryl substituents, or each $R^3$ is a siloxane having the structure $—(CR^1_2)_e—[SiR^4_2—O]_f—SiR^4_2—(CR^1_2)_g—$, in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50; and

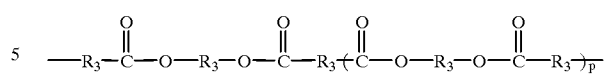
(v)

in which p is 1 to 100, each $R^3$ independently is an alkyl or alkyloxy chain having up to 100 atoms in the chain, which chain may contain aryl substituents, or each $R^3$ is a siloxane having the structure $—(CR^1_2)_e—[SiR^4_2—O]_f—SiR^4_2—(CR^1_2)_g—$ in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50;

(d) K is an aromatic group selected from group of aromatic groups having the structures:

(VI)

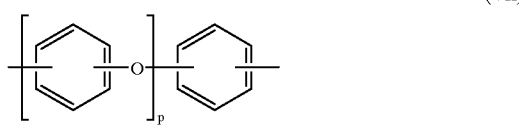
(VII)

in which p is 1 to 100;

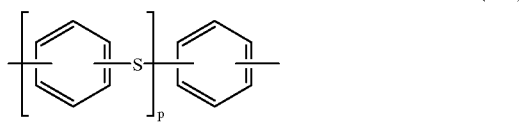
(VIII)

in which p is 1 to 100;

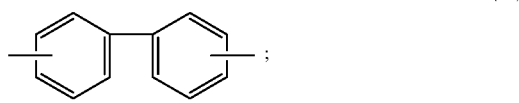
(IX)

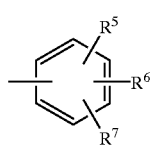
(X)

in which $R^5$, $R^6$, and $R^7$ are a linear or branched chain alkyl, alkyloxy, alkyl amine, alkyl sulfide, alkylene, alkyleneoxy, alkylene amine, alkylene sulfide, aryl, aryloxy, or aryl sulfide species having up to about 100 atoms in the chain, which may contain saturated or unsaturated cyclic or heterocyclic substituents pendant from the chain or as part of the backbone in the chain, and in which any heteroatom present may or may not be directly attached to the aromatic ring; or $R^5$, $R^6$, and $R^7$ are a siloxane having the structure $-(CR^1_2)_e-[SiR^4_2-O]_f-SiR^4_2-(CH_3)_g-$ in which the $R^1$ substituent is H or an alkyl group having 1 to 5 carbon atoms and the $R^4$ substituent independently for each position is an alkyl group having 1 to 5 carbon atoms or an aryl group, and e is 1 to 10 and f is 1 to 50;

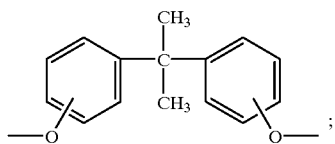

(XI)

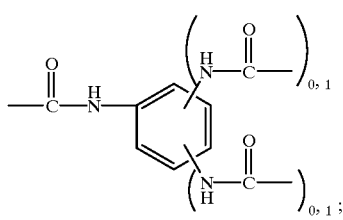

(XII)

and

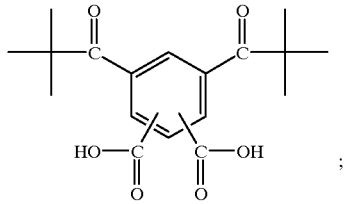

(XIII)

and (e) Z is selected from the group consisting of
(i)

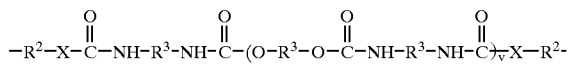

(i)

in which each $R^2$ independently is an alkyl, aryl, or arylalkyl group having 1 to 18 carbon atoms; $R^3$ is an alkyl or alkyloxy chain having up to 100 atoms in the chain, which chain may contain aryl substituents; X is O, S, N, or P; and v is 0 to 50;

$-(CR^1_2)_e-[SiR^4_2-O]_f-SiR^4_2-(CR^1_2)_g-$ (ii)

in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50;

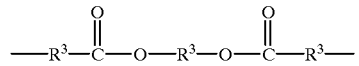

(iii)

in which $R^3$ is an alkyl or alkyloxy chain having up to 100 atoms in the chain, which chain may contain aryl substituents;

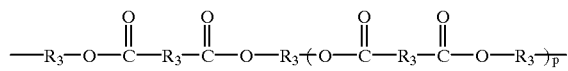

(iv)

in which p is 1 to 100, each $R^3$ is independently an alkyl or alkyloxy chain having up to 100 atoms in the chain, which chain may contain aryl substituents, or each $R^3$ is a siloxane having the structure $-(CR^1_2)_e-[SiR^4_2-O]_f-SiR^4_2-(CR^1_2)_g-$ in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50, and

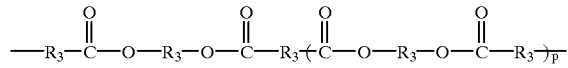

(v)

in which p is 1 to 100, each $R^3$ independently is an alkyl or alkyloxy chain having up to 100 atoms in the chain, which chain may contain aryl substituents, or each $R^3$ is a siloxane having the structure $-(CR^1_2)_e-[SiR^4_2-O]_f-SiR^4_2-(CR^1_2)_g-$ in which the $R^1$ substituent independently for each position is H or an alkyl group having 1 to 5 carbon atoms, the $R^4$ substituent independently for each position is an alkyl group having 1 to 5 carbon atoms or an aryl group, e and g are independently 1 to 10, and f is 1 to 50.

2. A die attach adhesive comprising an allylated amide compound having the formula

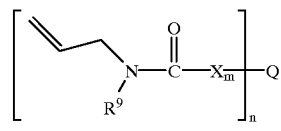

or

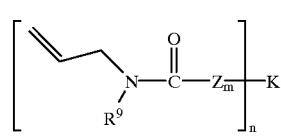

according to claim 1.

* * * * *